Figure 1:
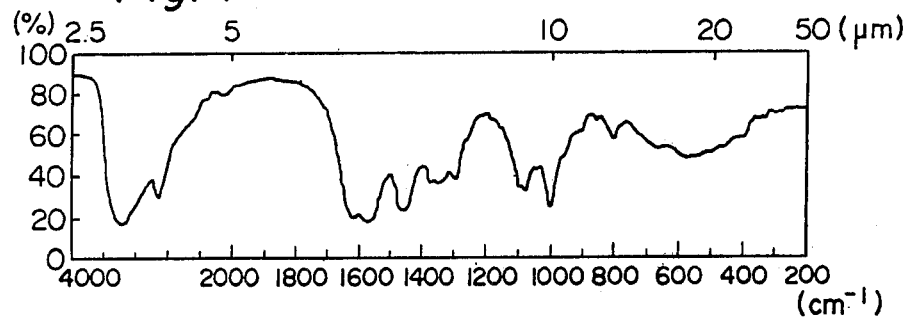

United States Patent [19]

Mori et al.

[11] 4,389,486
[45] Jun. 21, 1983

[54] BIOLOGICALLY PURE CULTURE

[75] Inventors: Toshihito Mori; Takeo Deushi; Akio Iwasaki; Takafumi Kunieda; Toshimi Mizoguchi; Kazuhiro Kamiya; Masahoto Nakayama, all of Higashimurayama; Hisakatsu Ito, Kawagoe; Takeshi Oda, Kodaira, all of Japan

[73] Assignee: Kowa Company, Ltd., Japan

[21] Appl. No.: 316,526

[22] Filed: Oct. 29, 1981

Related U.S. Application Data

[62] Division of Ser. No. 955,412, Oct. 26, 1978, Pat. No. 4,328,307, which is a division of Ser. No. 888,149, Mar. 16, 1978, Pat. No. 4,206,206.

[30] Foreign Application Priority Data

Mar. 24, 1977 [JP] Japan ................................. 52-31580
Nov. 8, 1977 [JP] Japan ................................. 52-133051

[51] Int. Cl.³ ............................................... C12N 1/20
[52] U.S. Cl. ................................................... 435/253
[58] Field of Search .................................. 435/253, 80

[56] References Cited

U.S. PATENT DOCUMENTS 3,931,400  1/1976  Nara et al. ........................ 435/79
4,028,188  6/1977  Daum et al. ....................... 435/80

*Primary Examiner*—Alvin E. Tanenholtz
*Attorney, Agent, or Firm*—Wenderoth, Lind & Ponack

[57] ABSTRACT

Novel antibiotics of the following structure

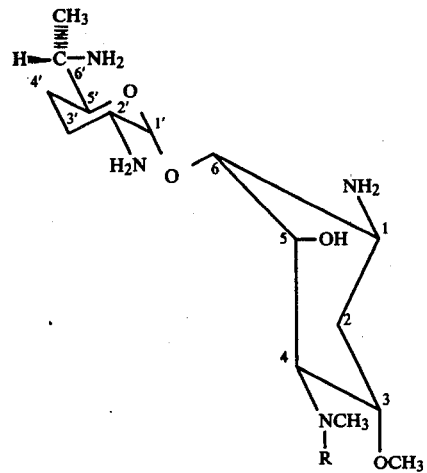

wherein R represents a moiety selected from the group consisting of hydrogen, $-COCH_2NH_2$, $-COCH_2NH-CONH_2$ and $-COCH_2NHCHO$; process for preparation thereof; and biologically pure culture for use therein.

1 Claim, 4 Drawing Figures

BIOLOGICALLY PURE CULTURE

This is a divisional of Ser. No. 955,412, filed Oct. 26, 1978, now U.S. Pat. No. 4,328,307 which is a divisional of Ser. No. 888,149, filed Mar. 16, 1978, now U.S. Pat. No. 4,206,206.

This invention relates to novel antibiotics, a process for preparation of the antibiotics, and biologically pure culture for use in the process.

The present inventors have isolated various microorganisms from soil in search of antibiotics produced by these microorganisms. Consequently, they have succeeded in isolating an antibiotic-producing strain belonging to the genus Saccharopolyspora from the soil at Kobe, Japan. From its bacteriological properties described hereinbelow, the strain was assumed to be a natural mutant of *Saccharopolyspora hirsuta,* and termed *Saccharopolyspora hirsuta* KC-6606. This KC-6606 strain was deposited as FERM-P No. 3912 in Fermentation Research Institute, Agency of Industrial Science & Technology, Japan; as ATCC 20501 in American Type Culture Collection.

It has been ascertained that the antibiotics produced by the KC-6606 strain are substances not described in the literature and having an antibacterial action against Gram positive bacteria, Gram negative bacteria and acid-fast bacteria. This substance was termed "KA-6606 substance." It has also been found that by treatment with a pharmaceutically acceptable inorganic or organic acid, the novel antibiotic KA-6606 substance can be easily converted to an antibiotic in the form of an acid addition salt. Further investigation has led to the discovery that the KA-6606 substance can be further separated into four antibiotics, KA-6606 I, KA-6606 II, KA-6606 III, and KA-6606 IV, and the KA-6606 I, KA-6606 III and KA-6606 IV can be readily converted to KA-6606 II by treatment with alkalies or acids.

It is an object of this invention therefore to provide a novel antibiotic substance KA-6606, and its acid addition salts.

Another object of this invention is to provide a process for preparing the KA-6606 substance.

Still another object of the invention is to provide an antibiotic composition comprising the KA-6606 substance as an active ingredient.

A further object of the invention is to provide a biologically pure culture useful for providing the KA-6606 substance.

The above and other objects of this invention along with its advantages will become more apparent from the following description.

The antibiotics KA-6606 substance of this invention can be expressed by the following structural formula

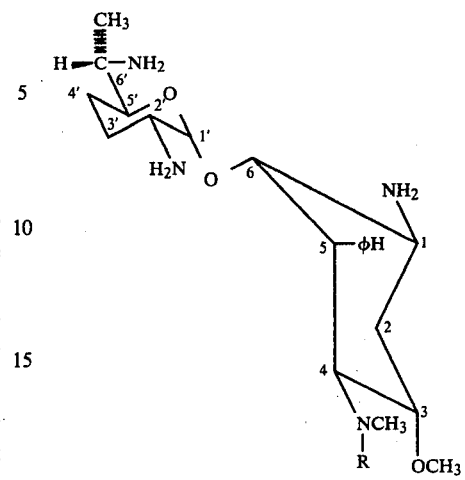

(Structure I)

wherein R represents a moiety selected from the group consisting of hydrogen, —COCH$_2$NH$_2$, —COCH$_2$NHCONH$_2$ and —COCH$_2$NHCHO. KA-6606 II is a compound of structure (1) wherein R is hydrogen; KA-6606 I is a compound of structure (1) wherein R is —COCH$_2$NH$_2$; KA-6606 III is a compound of structure (1) wherein R is —COCH$_2$NHCONH$_2$; and KA-6606 IV is a compound of structure (1) wherein R is —COCH$_2$NHCHO. The KA-6606 substance of structure (1) which is produced by fermentation the KA-6606 substance-producing strain of the genus Saccharopolyspora and accumulated in the culture broth contains the four substances described above. If desired, it can be separated into these four substances or into mixtures containing two or three of these substances. These substances are useful as antibiotics either singly or as such mixtures. Treatment of the KA-6606 I, KA-6606 III and KA-6606 IV with alkalies or acids yields KA-6606 II of structure (I) in which R is hydrogen.

The chemical structures and physical and chemical properties of the KA-6606 I, II, III and IV are described below.

KA-6606 I can be expressed by the following structural formula

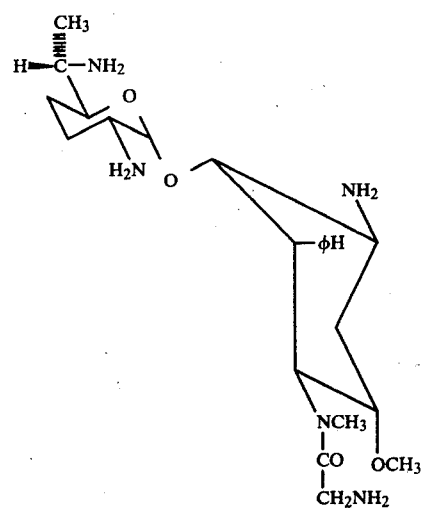

Structure (1-a)

and has the following molecular formula, specific rotation and melting point.

Molecular formula: $C_{17}H_{35}O_5N_5$

Specific rotation: $[\alpha]_D^{27} + 104°$ (c 1, $H_2O$)

Melting point: 125°–135° C.

KA 6606 II can be expressed by the following structural formula

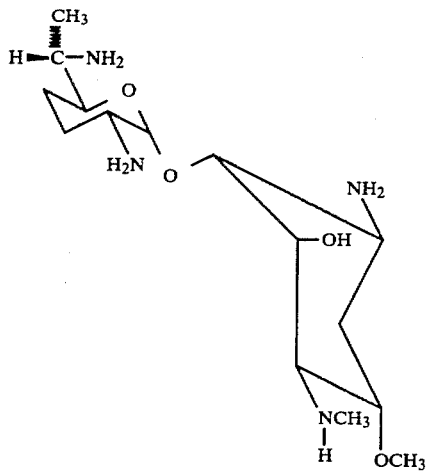
Structure (1-b)

and has the following molecular formula, specific rotation and melting point.

Molecular formula: $C_{15}H_{32}O_4N_4$

Specific rotation: $[\alpha]_D^{27} + 139.5°$ (c 1, $H_2O$)

Melting point: 88°–95° C.

KA-6606 III can be expressed by the following structural formula

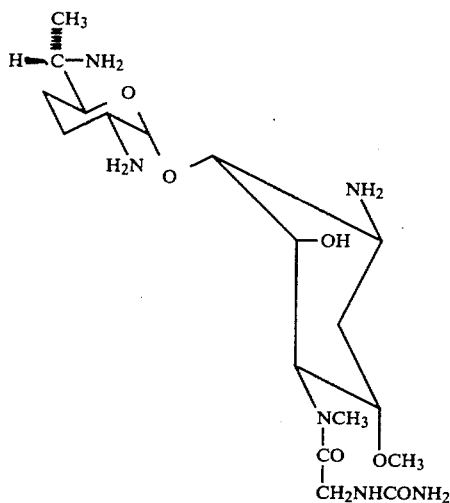
Structure (1-c)

and the following molecular formula, specific rotation and melting point.

Molecular formula: $C_{18}H_{36}O_6N_6$

Specific rotation: $[\alpha]_D^{27} + 103°$ (c 1, $H_2O$)

Melting point: 145°–152° C.

KA-6606 IV can be expressed by the following structural formula

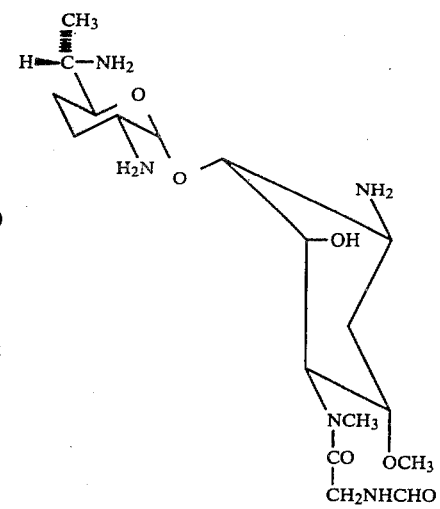
Structure (1-d)

and has the following molecular formula, specific rotation and melting point.

Molecular formula: $C_{18}H_{35}O_6N_5$

Specific rotation: $[\alpha]_D^{27} + 101°$ (c 1, $H_2O$)

Melting point: 135°–140° C.

Known antibiotics which are most similar to the antibiotic substances KA-6606 of formula (1) are fortimicin A, B and C [see Japanese Laid-Open Patent Publications Nos. 6487/78 (published on Jan. 20, 1978), 29789/75 (published on Mar. 25, 1975), 145588/75 (published on Nov. 21, 1975), 18888/77 (published on Feb. 12, 1977) and 83513/77 (published on July 12, 1977), and Japanese Patent Publication No. 46311/77 (published on Nov. 24, 1977)]. Fortimicin is an antibiotic produced by Micromonospora sp. MK-70 strain (FERM-P No. 1560; ATCC 21819), and as disclosed in The Journal of Antibiotics, Vol. XXX, No. 7, pp. 552–563, has a different chemical structure from the KA-6606 substance of formula (1) given above in that the KA-6606 substance does not have a hydroxyl group at the 2-position and has a different configuration of an amino group at the 1-position.

As will be described hereinbelow, the KA-6606 substance of this invention has a better antibacterial activity than fortimicin.

The novel antibiotic of the invention can be produced by fermenting the antibiotic KA-6606-producing strain of the genus Saccharopolyspora and isolating the antibiotic KA-6606 substance from the culture broth. If desired, one or more of the antibiotics KA-6606 I, KA-6606 II, KA-6606 III and KA-6606 IV can be separated from the resulting KA-6606 substance.

The taxonomic characterization of *Saccharopolyspora hirsuta* KC-6606, a typical example of the KA-6606-producing strain, is shown below. Unless otherwise specified, its properties on various culture media were observed by ordinary methods after cultivating it for 21 days at 27° C. The colors were expressed for mature culture in accordance with the classifications of "Color Harmony Manual" (Container Corp. Amer. 1958).

I. Morphological Properties

This strain forms substrate hyphae and aerial hyphae on an inorganic salts-starch agar medium. The substrate hyphae (0.5 to 0.7μ in diameter) spread out in long branches and are tangled with each other complicately, permitting usually one, very rarely 2 to 3, substrate spore like bodies (0.8 to 1.2μ in diameter) to adhere to the end of the sporangiophore (about 2.5μ in length). Occasionally typical nocardioform fragmentation is found in the colony. The aerial hyphae (0.6 to 0.9μ in diameter) are short, and the mature spores are observed as chains of 20 or more spores and segmented into beadlike chains of spores often separated by the length of empty hyphae. The spore chains are observed as loops and loose spirals. The spores are oval to short cylindrical (0.5–0.6μ×0.7–0.9μ), and the surfaces of the spores are covered with a sheath having a hairy structure.

II. Properties on Various Media
1. Sucrose-nitrate agar
   Growth: good
   Aerial hyphae: good, powdery, shell pink (5ba)
   Substrate hyphae: butyrous, light tan to rose beige (3gc–4gc)
   Soluble pigment: pale pink with a tint of yellowish brown
2. Glycerol-nitrate agar
   Growth: moderate to good
   Aerial hyphae: good, powdery, white (a)
   Substrate hyphae: butyrous, light ivory (2ca)
   Soluble pigment: pale yellow
3. Glucose-asparagine agar (slant)
   Growth: moderate
   Aerial hyphae: none
   Substrate hyphae: butyrous to gelatinous, buff (2fb)
   Soluble pigment: slightly pale yellow
4. Glycerol-aspraragine agar (ISP medium No. 5)
   Growth: moderate
   Aerial hyphae: poor, powdery, white (a)
   Substrate hyphae: gelatinous, light ivory (2ca)
   Soluble pigment: slightly pale yellow
5. Inorganic salts-starch agar (ISP medium No. 4)
   Growth: good
   Aerial hyphae: poor, powdery, white (a)
   Substrate hyphae: cartilaginous, light ivory to buff (2ca–2fb)
   Soluble pigment: none
6. Tyrosine agar (slant, ISP medium No. 7)
   Growth: moderate
   Aerial hyphae: good, powdery, white (a)
   Substrate hyphae: butyrous to gelatinous, light ivory to buff (2ca–2fb)
   Soluble pigment: slightly pale yellow
7. Nutrient agar
   Growth: moderate
   Aerial hyphae: none
   Substrate hyphae: gelatinous, buff (2fb)
   Soluble pigment: none
8. Yeast extract-malt extract agar (ISP medium No. 2)
   Growth: good
   Aerial hyphae: sparse, powdery, white (a)
   Substrate hyphae: gelatinous, bamboo (2g)
   Soluble pigment: pale yellow
9. Oatmeal agar (ISP medium No. 3)
   Growth: poor
   Aerial hyphae: none
   Substrate hyphae: colorless
   Soluble pigment: none
10. Peptone-yeast extract-iron agar (slant, ISP medium No. 6)
    Growth: moderate
    Aerial hyphae: poor, powdery, white (a)
    Substrate hyphae: butyrous to gelatinous, light melon yellow (2ea)
    Soluble pigment: slightly pale yellow
11. Bennett's agar
    Growth: good
    Aerial hyphae: none
    Substrate hyphae: gelatinous, light ivory (2ca)
    Soluble pigment: slightly pale yellow III. Physiological Properties
1. Growth temperature: 18°–45° C.
2. Liquefaction of gelatin: positive
3. Hydrolysis of starch: positive
4. Action on milk:
   Coagulation: negative
   Peptonization: positive
5. Production of melanoid pigment:
   Negative in tyrosine agar and in peptone-iron-yeast extract agar.
6. Production of nitrite from nitrate and its accumulation: positive IV. Utilization of Carbon Sources
Positive: D-glucose, D-fructose, raffinose, sucrose, D-mannitol, galactose, inulin, and salicin.
Negative: L-arabinose, D-xylose, inositol, L-rhamnose, sorbitol, lactose, and dulcitol.

As described above, the KC-6606 strain forms substrate hyphae and aerial hyphae on various agar media. The substrate spore like-bodies adhere to the substrate hyphae, and the spore chains adhere to the substrate hyphae. The substrate hyphae occasionally fragment into rod-shaped elements. The surfaces of the spores are covered with a sheath having hairy structure.

Analysis of its cell wall showed that it contains mes-diaminopimelic acid and arabinose and galactose as sugars. Accordingly, the cell wall of this strain is believed to be of type IV.

Analysis of the fatty acids in the cell wall showed that it does not contain LCN-A (lipid characteristic of nocardia).

Known strains having these characteristics have been searched through Bergey's Manual of Determinative Bacteriology, 8th edition (1975). As a result, it has been found that the genus Micropolyspora is a similar genus, and the genus Saccharopolyspora reported by Lacey and Goodfellow (Journal of General Microbiology, Vol. 88, page 75, 1975) can also be cited as a similar strain. The strain used in this invention differs from strains of the genus Micropolyspora in that it has a hairy structure in spores and the spore chains contains more than 20 spores. But it is similar in morphology to the latter. This leads to the belief that the KC-6606 strain belongs to the genus Saccharopolyspora. There has been no established method for the systematic classification of the genus Saccharopolyspora because only one species for one genus has been reported.

The differences between the KC-6606 strain and the *Saccharopolyspora hirsuta* are shown in Table 1.

TABLE 1

|  | KC-6606 | Saccharopolyspora hirsuta |
|---|---|---|
| Utilization of sugars |  |  |
| Xylose | − | + |
| Rhamnose | − | + |
| Sorbitol | − | + |
| Inositol | − | + |
| Production and accumulation of nitrite | + | − |

Since the KC-6606 strain and *Saccharopolyspora hirsuta* correspond well with each other in basic properties such as morphology, properties on various culture media and physiological properties although differing in the utilization of carbon sources and the formation and accumulation of nitrite, it would be reasonable to consider that these strains belong to the same species.

On the basis of the above information, the present inventors have considered the strain in question as a natural mutant of Saccharopolyspora, and named it Saccharopolyspora hirsuta KC-6606 strain. The strain of Saccharopolyspora hirsuta used in this invention is susceptible to change in its characteristics, and can be mutated easily by an artificial mutating means using ultraviolet rays, X-rays, various chemicals such as nitrosoguanidines or mitomycin, etc. All such mutants which have the ability to produce the antibiotic KA-6606 substance can be used in this invention. In this regard, the ability of strains belonging to Saccharopolyspora hirsuta to produce antibiotics has not been reported.

According to this invention, there is provided a biologically pure culture of Sacchropolyspora hirsuta KC-6606 having characteristics identified as FERM-P No. 3912, and ATCC 20501, and also having the ability to produce antibiotic KA-6606 substance by fermentation in an aqueous nutrient medium containing a carbon source, a nitrogen source and minerals.

Suitable culture media for use in fermenting the KA-6606 substance-producing strain of the genus Saccharopolyspora comprise carbon and nitrogen sources and as optional ingredients, inorganic salts (minerals), very small amounts of heavy metals, etc.

Various carbon sources can be used, and examples of preferred carbon sources are starch, glycerol, maltose, dextrin, sucrose, fructose and molasses, which can be used either alone or as suitable mixtures. Hydrocarbons, organic acids and vegetable oils can also be used if the particular strain can utilize them as a carbon source. Examples of nitrogen sources are soybean meal, yeast extract, dried yeast, peptone, meat extract, corn steep liquor, Casamino acid, Distiller's soluble, ammonium chloride, ammonium sulfate, urea and sodium nitrate, which can be used either alone or as suitable mixtures. Examples of inorganic salts include sodium chloride, potassium phosphate, magnesium sulfate, calcium chloride, calcium carbonate, calcium hydroxide, cobaltic chloride, zinc sulfate, ferric chloride, and ferrous sulfate.

Inorganic substances and organic substances (e.g., amino acids) which aid in the growth of the strain and promote the production of KA-6606 substance can also be added to the culture medium as required. When an aerating cultivation method is employed, an antifoamer such as fatty acid oils, silicon oils and paraffins can also be added to the culture medium.

Cultivation may be carried out in a solid medium. Preferably, however, same as in the general process for producing antibiotics, a liquid cultivating method, especially a submerged cultivation method, is used. The cultivation is carried out under aerobic conditions, and the cultivation temperature is generally about 20° to about 40° C., preferably about 27° C. Preferably, during the cultivation, the pH of the culture medium is maintained at about 4 to about 10. The cultivation period is generally about 2 days to about 6 days.

As a result of the cultivation, the KA-6606 substance is produced and accumulated in the culture broth. When the amount of the KA-6606 substance produced in the culture broth reaches a maximum, the cultivation is stopped, and the KA-6606 substances can be collected from the culture broth.

Since the KA-6606 substance is a water-soluble basic substance soluble in water but only slightly soluble in common organic solvents, it can be separated from the culture broth by utilizing means which are customarily used in isolating and purifying water-soluble basic antibiotics. For example, there can be used an adsorption desorption method using an ion exchange resin, active carbon, cellulose, silica gel, alumina, and a method for extracting with butanol, amyl alcohol, etc. using a higher fatty acid as an adjuvant.

For example, if the culture broth filtrate is charged into a column of a weak acidic cation exchange resin, the KA-6606 substance is adsorbed to it. The KA-6606 substance is then isolated by elution with a 0.1–3.0 N alkali or acid or various salt solutions. The resulting active eluate is lyophilized to afford a crude powder of KA-6606 substance.

Examples of the weak acidic cation exchange resin used to recover the KA-6606 substance are Amberlite IRC-50, IRC-84 and CG-50 (Rohm & Haas Co.); and Dianion WK-10 and WK-20 (Mitsubishi Chemical Co., Ltd.). Alkalies that can be used for the elution are ammonium hydroxide solution, and an aqueous solution of sodium hydroxide. Examples of the acids are formic acid, hydrochloric acid and sulfuric acid. The salt solutions may, for example, be a solution of ammonium carbonate and a solution of ammonium formate. Another example of the recovering method comprises adjusting the pH of the culture broth filtrate to 7 to 9, contacting the filtrate with active carbon to cause the KA-6606 to adsorb to the active carbon, and eluting the substance with acidic water or hydrochloric acid-methanol.

The KA-6606 substance that can be isolated by the methods described above can be separated into KA-6606, I, II, III and IV by dissolving it in water or dilute ammonium hydroxide, charging it into a column of an adsorbent such as a weak acidic ion exchange resin of the type described above or a weak acidic ion exchanger such as CM-sephadex or CM cellulose to cause the substance to be adsorbed to the adsorbent, and then eluting it with an alkaline aqueous solution such as dilute ammonium hydroxide, or an aqueous solution of ammonium carbonate or ammonium formate by a gradient method or a stepwise method. According to this separating procedure, first several components in trace amounts are eluted, and then KA-6606 IV and KA-6606 III as free bases are eluted in this order. On further elution, KA-6606 I and KA-6606 II are separated successively.

The resulting KA-6606 I, II, III and IV can be purified by chromatography on cellulose, silica gel, Sephadex (e.g. LH 20), etc. For example, it can be chromatographed on a silica gel column using a mixture (1:8:3) of chloroformmethanol-17% ammonium hydroxide as an eluent.

The KA-6606 I, II, III and IV that can be separated by the method described above are in the form of free bases, and as desired, may be obtained in the form of a pure free base by causing them to be adsorbed to a column of a strong base anion exchange resin such as Dowex 1×2 (Dow Chemical), eluting them with deionized water, collecting active fractions, and lyophilizing the collected fractions.

These KA-6606, I, II, III and IV obtained as free bases can be converted to their acid addition salts by treatment with pharmaceutically acceptable inorganic or organic acids. Examples of such acids are inorganic acids such as hydrochloric acid, sulfuric acid and hydrobromic acid, and organic acids such as acetic acid and oxalic acid.

The KA-6606 I, KA-6606 III and KA-6606 IV can be converted to KA-6606 II by treatment with alkalies or acids. The conversion can be effected by treating the KA-6606 I, KA-6606 III and KA-6606 IV with a 0.1–4 N aqueous solution of an alkaline reagent such as sodium hydroxide or barium hydroxide or with a 0.1–1 N aqueous solution of an acidic reagent such as hydrochloric acid or sulfuric acid.

In the case of using the alkaline reagent, a strong base anion exchange resin [e.g., Amberlite IRA 400 (OH⁻ form) or Dowex 1×2 (OH⁻ form)] may be added, and the reaction can be performed in the suspended state. Likewise, when the acidic reagent is used, a strong acidic cation exchange resin such as Amberlite 1R 120 (H⁺ form) or Dowex 50×8 (H⁺ form) may be added, and the reaction can be performed in the suspended state. The reaction can be performed usually at about 30° to 100° C. for about 0.5 to 3 hours.

The physical and chemical properties of the novel antibiotics KA-6606 I, II, III and IV of structures (1-a) to (1-d) are described below.

KA-6606 1 (free base)

(1) Nature: white powder
(2) Molecular formula: $C_{17}H_{35}O_5N_5$
(3) Elemental analysis:

|  | C | H | N |
|---|---|---|---|
| Found (%): | 52.10 | 8.84 | 17.83 |
| Calculated (%): | 52.42 | 9.06 | 17.99 |

(4) Molecular weight: 389 (mass spectrum)
(5) Melting point: 125°–135° C.
(6) Specific rotation: $[\alpha]_D^{27}+104°$ (c 1, H₂O)
(7) Ultraviolet absorption spectrum At 220–360 nm, so characteristic absorption is shown, but only a terminal absorption exists.

(8) Infrared absorption spectrum

The infrared absorption spectrum of a sample in potassium bromide tablet is as shown in FIG. 1.

(9) Solubility

Very readily soluble in water. Easily soluble in methanol, slightly soluble in ethanol. Insoluble in chloroform, ethyl acetate, diethyl ether, hexane and petroleum ether.

(10) Color reaction

Ninhydrin reaction and Rydon Smith reaction: positive; Sakaguchi reaction, maltol reaction, ferric chloride reaction and Fehling reaction: negative

(11) Stability

Stable at a pH of 3 to 8; gradually decomposed and inactivated in basicity and strong acidicity.

(12) Nuclear magnetic resonance spectrum ($\delta_{D2O}$, ppm):

1.25 (3H, d, C—C$\underline{H}_3$)
3.05 (3H, s, N—C$\underline{H}_3$)
3.07 (2H, s, COC$\underline{H}_2$N)
3.40 (3H, s, OC$\underline{H}_3$)
5.00 (1H, d, anomeric $\underline{H}$)

(13) Mass spectrum (m/e): 389(M⁺), 276, 258, 248, 230, 180, 143

(14) Paper chromatography
  Rf value: 0.53
  Filter paper: Whatman No. 1
  Solvent: a lower layer of chloroform-methanol-17% ammonium hydroxide (2:1:1)

(15) Thin-layer chromatography

| Rf value | Solvent |
|---|---|
| 0.56 | Butanol-ethanol-chloroform-17% ammonium hydroxide (4:2:5:2) |
| 0.60 | Chloroform-methanol-17% ammonium hydroxide (1:8:3) |
| 0.10 | A lower layer of chloroform-methanol-17% ammonium hydroxide (2:1:1) |
| 0.76 | An upper layer of chloroform-methanol-17% ammonium hydroxide (2:1:1) |

TLC aluminum sheet (silica gel 60 $F_{254}$ 0.2 mm) (Merck) was used.

Tetra-N-acetyl derivative of KA-6606 I substance (1) Nature: colorless crystalline powder
(2) Molecular formula: $C_{25}H_{43}O_9N_5$
(3) Elemental analysis:

|  | C | H | N |
|---|---|---|---|
| Found (%): | 53.51 | 7.58 | 12.44 |
| Calculated (%): | 53.85 | 7.77 | 12.56 |

(4) Molecular weight: 557 (mass spectrum)
(5) Melting point: 160°–166° C.
(6) Specific rotation: $[\alpha]_D^{25}+112°$ (c 1, H₂O)
(7) Nuclear magnetic resonance spectrum ($\delta_{D2O}$, ppm):

1.10 (3H, d, C—C$\underline{H}_3$)
1.95, 2.00, 2.05, 2.07 (3H, s, COC$\underline{H}_3$)
3.09 (3H, s, N—C$\underline{H}_3$)
3.42 (3H, s, O—C$\underline{H}_3$)
4.11 (2H, s, COC$\underline{H}_2$N)
4.95 (1H, d, anomeric H)

(8) Mass spectrum (m/e): 557(M⁺), 342, 314, 296, 227

KA-6606 II substance (free base)

(1) Nature: white powder
(2) Molecular formula: $C_{15}H_{32}O_4N_4$
(3) Elemental analysis:

|  | C | H | N |
|---|---|---|---|
| Found (%): | 53.97 | 9.51 | 16.55 |
| Calculated (%): | 54.19 | 9.70 | 16.85 |

(4) Molecular weight: 332 (mass spectrum)
(5) Melting point: 88°–95° C.
(6) Specific rotation: $[\alpha]_D^{27}+139.5°$ (c 1, H₂O)
(7) Ultraviolet absorption spectrum At 220 to 360 nm, no specific absorption is shown, but only a terminal absorption exists.

(8) Infrared absorption spectrum

Figure 2:
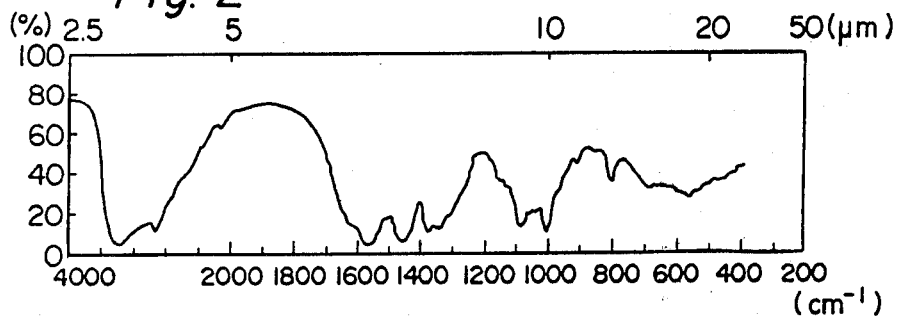

The infrared absorption spectrum of a sample in potassium bromide tablet is as shown in FIG. 2.

(9) Solubility

Very readily soluble in water; easily soluble in methanol; slightly soluble in ethanol; insoluble in chloroform, ethyl acetate, diethyl ether, hexane and petroleum ether.

(10) Color reaction

Ninhydrin reaction and Rydon Smith reaction: positive; Sakaguchi reaction, maltol reaction, ferric chloride reaction and Fehling reaction: negative

(11) Stability

Stable at a pH of at least 2; gradually decomposed and inactivated in strong acidity.

(12) Nuclear magnetic resonance spectrum ($\delta_{D_2O}$, ppm):
 1.25 (3H, d, C—C$\underline{H}_3$)
 2.70 (3H, s, N—C$\underline{H}_3$)
 3.45 (3H, s, O—C$\underline{H}_3$)
 4.95 (1H, d, anomeric H)

(13) Mass spectrum (m/e): 332(M+), 283, 219, 119, 143

(14) Paper chromatography
 Rf value: 0.86
 Filter paper: Whatman No. 1
 Solvent: a lower layer of chloroform-methanol-17% ammonium hydroxide (2:1:1)

(15) Thin-layer chromatography

| Rf value | Solvent |
|---|---|
| 0.57 | Butanol-ethanol-chloroform-17% ammonium hydroxide (4:5:2:5) |
| 0.52 | Chloroform-methanol-17% ammonium hydroxide (1:8:3) |
| 0.16 | A lower layer of chloroform-methanol-17% ammonium hydroxide (2:1:1) |
| 0.80 | An upper layer of chloroform-methanol-17% ammonium hydroxide (2:1:1) |

TLC aluminum sheet (silica gel 60 F$_{254}$ 0.2 mm) (Merck Co.) was used as the plate.

Penta-N-acetyl derivative of KA-6606 II substance (1) Nature: colorless needle
(2) Molecular formula: $C_{23}H_{40}O_8N_4 \cdot H_2O$
(3) Elemental analysis:

| | C | H | N |
|---|---|---|---|
| Found (%): | 52.99 | 7.65 | 10.52 |
| Calculated (%): | 53.27 | 8.16 | 10.80 |

(4) Molecular weight: 500 (mass spectrum)
(5) Melting point: 139°–141° C.
(6) Specific rotation: $[\alpha]_D^{22} + 52°$ (c 1, H$_2$O)
(7) Nuclear magnetic resonance spectrum ($\delta_{D_2O}$, ppm):
 1.09 (3H, d, C—C$\underline{H}_3$)
 1.98, 1.99, 2.01, 2.13 (3H, s, CO—C$\underline{H}_3$)
 3.10 (3H, s, N—C$\underline{H}_3$)
 3.40 (3H, s, O—C$\underline{H}_3$)
 4.96 (1H, d, anomeric H)

(8) Mass spectrum (m/e): 500(M+), 303, 271, 257, 227

KA-6606 III substance (free base)

(1) Nature: white powder
(2) Molecular formula: $C_{18}H_{36}O_6N_6$
(3) Elemental analysis:

| | C | H | N |
|---|---|---|---|
| Found (%): | 49.51 | 8.11 | 19.10 |
| Calculated (%): | 49.99 | 8.39 | 19.43 |

(4) Molecular weight: 432 (mass spectrum)
(5) Melting point: 145°–152° C.
(6) Specific rotation: $[\alpha]_D^{27} + 103°$ (c 1, H$_2$O)
(7) Ultraviolet absorption spectrum At 220 to 360 nm, no specific absorption is shown, but only a terminal absorption exists.

(8) Infrared absorption spectrum

Figure 3:
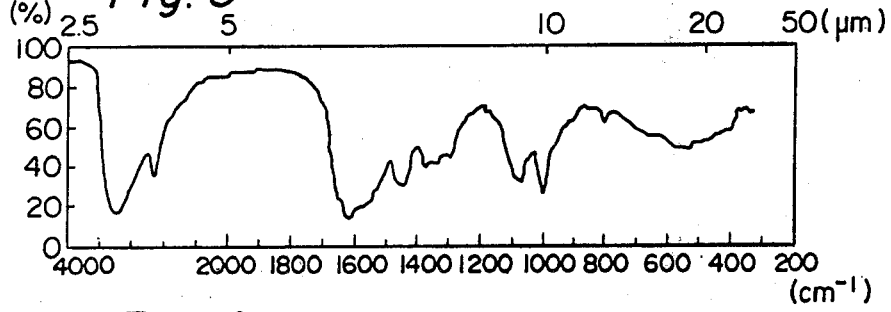

The infrared absorption spectrum of a sample in potassium bromide tablet is as shown in FIG. 3.

(9) Solubility

Very readily soluble in water; easily soluble in methanol; slightly soluble in ethanol; insoluble in chloroform, ethyl acetate, diethyl ether, hexane, and petroleum ether.

(10) Color reaction

Ninhydrin reaction, and Rydon Smith reaction: positive; Sakaguchi reaction, maltol reaction, ferric chloride reaction, Fehling reaction: negative

(11) Stability

Stable at a pH of 3 to 8; gradually decomposed and inactivated in basicity and strong acidity.

(12) Nuclear magnetic resonance spectrum ($\delta_{D_2O}$, ppm):
 1.21 (3H, d, C—C$\underline{H}_3$)
 3.07 (3H, s, N—C$\underline{H}_3$)
 3.40 (3H, s, O—C$\underline{H}_3$)
 4.06 (2H, s, CO—C$\underline{H}_2$—N)
 4.95 (1H, d, anomeric $\underline{H}$)

(13) Mass spectrum (m/e): 432(M+), 273, 219, 194, 173, 143

(14) Paper chromatography:
 Rf value: 0.27
 Filter paper: Whatman No. 1
 Solvent: a lower layer of chloroform-methanol-17% ammonium hydroxide (2:1:1)

(15) Thin-layer chromatography

| Rf value | Solvent |
|---|---|
| 0.55 | Butanol-ethanol-chloroform-17% ammonium hydroxide (4:5:2:5) |
| 0.64 | Chloroform-methanol-17% ammonium hydroxide (1:8:3) |
| 0.06 | A lower layer of chloroform-methanol-17% ammonium hydroxide (2:1:1) |
| 0.77 | An upper layer of chloroform-methanol-17% ammonium hydroxide (2:1:1) |

TLC aluminum sheet (silica gel 60 F$_{254}$ 0.2 mm) (Merck) was used as the plate.

KA-6606 IV substance (free base)

(1) Nature: white powder
(2) Molecular formula: $C_{18}H_{35}O_6N_5$
(3) Elemental analysis:

| | C | H | N |
|---|---|---|---|
| Found (%): | 51.39 | 8.08 | 16.41 |
| Calculated (%): | 51.78 | 8.45 | 16.77 |

(4) Molecular weight: 417 (mass spectrum)
(5) Melting point: 135°–140° C.
(6) Specific rotation: $[\alpha]_D^{27} + 101°$ (c 1, H$_2$O)
(7) Ultraviolet absorption spectrum At 220 to 360 nm, no specific absorption is shown, but only a terminal absorption exists.

(8) Infrared absorption spectrum

TABLE 3-continued

|  | KA-6606 substances | | | | Fortimicin | |
|---|---|---|---|---|---|---|
|  | I | II | III | IV | A | Amikacin |
| Serratia sp. | 1.5 | 100 | 6 | 12 | 3 | 1.5 |
| Mycobacterium smegmatis 607 | 0.4 | >100 | >25 | 12 | 0.8 | 0.8 |

(I) 3'-phosphotransferase I
(II) 3'-phosphotransferase II
(III) 2''-nucleotidyltransferase
(IV) 6'-acetyltransferase
(V) 2'-acetyltransferase The acute toxicities of the KA-6606 I, II, III and IV of this invention determined by using mice are as follows.

|  | KA-6606 I | KA-6606 II | KA-6606 III | KA-6606 IV |
|---|---|---|---|---|
| $LD_{50}$ iv. | 50–100 | >400 | >200 | >200 |
| (mg/ sc. kg) | 200–400 | >1,000 | >800 | >800 |

According to this invention, there can also be provided an antibiotic composition comprising (1) an effective amount of at least one compound selected from the group consisting of the KA-6606 substances of this invention and pharmaceutically acceptable acid addition salts thereof, and (2) a pharmaceutically acceptable diluent or carrier.

The amount of the compound (1) is, for example, about 0.01 to about 99.5% by weight, based on the weight of the composition.

The antibiotic composition of this invention may be in any dosage forms usually employed, but injecting preparations and capsules are especially preferred.

Preferably, like known water-soluble basic antibiotics, an injectable is prepared by filling a lyophilized powder of the antibiotic into a vial, preferably together with a stabilizer, and in use, the contents of the vial are dissolved in a dissolving liquid for administration.

The diluent or carrier includes, for example, liquid diluents such as distilled water for injection and physiological isotonic solution, and solid carriers such as lactose, starch, white sugar, glucose, crystalline cellulose, calcium carbonate, kaolin, D-mannitol, magnesium metasilicate aluminate, calcium sulfate, calcium phosphate and bentonite. Addition of stabilizers such as acidic sodium bisulfite is also preferred.

The dosage of the antibiotic substance of this invention can be suitably selected, and is, for example, about 0.01 to about 100 mg/kg/day.

Thus, according to this invention, there can be provided antibiotic compositions for animals other than human, such as poultry, domesticated animals and cultivated fish, and antibiotic compositions for man. These compositions are useful as antibacterial agents having a broad antibacterial spectrum.

The KA-6606 substance of this invention is also useful as a material for producing its derivatives.

The following Examples illustrate the present invention in greater detail.

EXAMPLE 1

A culture medium was prepared from 3% of starch, 1.5% of soybean meal, 0.5% of corn steep liquor, 0.2% of yeast extract, 0.05% of magnesium sulfate, 0.3% of sodium chloride, 0.3% of calcium carbonate, 0.001% of cobaltic chloride hexahydrate and tap water, adjusted to a pH of 7.0, and sterilized. The KC-6606 strain was inoculated in the culture medium and cultivated at 27° C. for about 50 hours to form a first seed culture.

Two hundred milliliters of the first seed culture was transferred to a 200-liter fermentor containing 100 liters of the same sterile medium as above and 1% of cotton seed oil. The cultivation was carried out while agitating at 225 rpm at an air flow rate of 50 liters per minute at 27° C. for 4 days.

After the cultivation, sulfuric acid was added to the culture broth to adjust its pH to 2.0. Then, the culture broth was filtered with the use of Dicalyte (Dicalyte Orient Co.) as a filter aid. A dilute aqueous solution of sodium hydroxide was added to the filtrate to adjust its pH to 8.0, and passed through a column of a cation exchange resin, Amberlite IRC-50 ($NH_4^+$ form) (the effluent was discarded). After washing the resin column with deionized water, the active substance adsorbed was eluted with 1 N ammonium hydroxide. The activity of the eluate was determined by a paper disc method using an agar plate of Bacillus subtilis. The fractions having activity were combined, and concentrated to about 50 ml under reduced pressure. The concentrate was lyophilized to afford 8.8 g of a crude powder of KA-6606 substance.

Eight grams of the crude powder was dissolved in 50 ml of distilled water. After adjusting the pH to 7.0, the solution was passed through a column (3 × 150 cm) of a cation exchange resin, Amberlite CG-50 I ($NH_4^+$ form). After washing with deionized water, the active portions were obtained by gradient elution between 5 l of 0.01 N ammonium hydroxide and 5 l of 1 N ammonium hydroxide at a flow rate of 150 ml/hour, and all fractions, each containing 25 ml, were determined by the paper disc method. Fractions containing ingredients corresponding to KA-6606 I, fractions containing ingredients corresponding to KA-6606 II, fractions containing ingredients corresponding to KA-6606 III, and fractions containing ingredients corresponding to KA-6606 IV were respectively collected, and lyophilized to afford 80 mg of a crude powder containing KA-6606 I, 16 mg of a crude powder containing KA-6606 II, 120 mg of a crude powder containing KA-6606 III, and 794 mg of a crude powder containing KA-6606 IV, respectively.

The lyophilized KA-6606 I and KA-6606 II were respectively dissolved in water, and after adjusting the pH to 7.0, each of the solutions was passed through a column (1 × 150 cm) of an anion exchange resin, Dowex 1×2 ($OH^-$ form). The active portion was developed with deionized water and the active fractions were combined, and lyophilized to afford 40 mg of KA-6606 I as a pure free base, and 10 mg of KA-6606 II as a pure free base.

Figure 4:
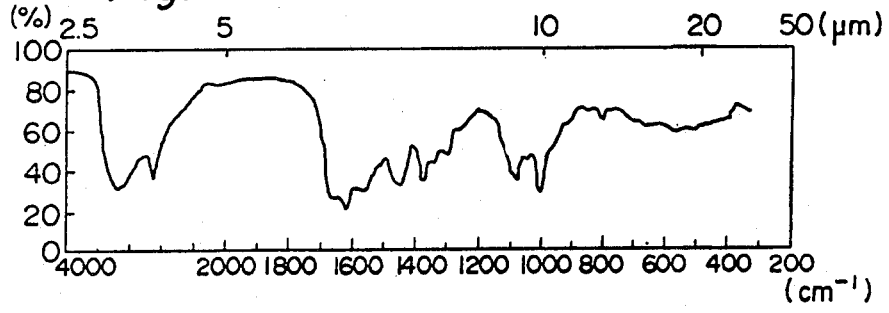

Separately, 120 mg of the crude powder containing KA-6606 III substance was dissolved in water, and the solution was passed through a column (2 × 60 cm) of silica gel packed with a solvent mixture of chloroform- The infrared absorption spectrum of a sample in potassium bromide tablet is as shown in FIG. 4.

(9) Solubility

Very readily soluble in water; easily soluble in methanol; slightly soluble in ethanol; insoluble in chloroform, ethyl acetate, diethyl ether, hexane and petroleum ether.

(10) Color reaction

Ninhydrin reaction, and Rydon Smith reaction: positive; Sakaguchi reaction, maltol reaction, ferric chloride reaction and Fehling reaction: negative

(11) Stability

Stable at a pH of 3 to 8; gradually decomposed and inactivated in basicity and strong acidity.

(12) Nuclear magnetic resonance spectrum ($\delta_{D_2O}$, ppm):

1.23 (3H, d, C—C$\underline{H}_3$)
3.09 (3H, s, N—C$\underline{H}_3$)
3.40 (3H, s, O—C$\underline{H}_3$)
4.18 (2H, s, CO—C$\underline{H}_2$—N)
5.03 (1H, d, anomeric $\underline{H}$)

(13) Mass spectrum (m/e): 417(M+), 304, 276, 258, 219, 173, 143

(14) Paper chromatography

Rf value: 0.55
Filter paper: Whatman No. 1
Solvent: a lower layer of chloroform-methanol-17% ammonium hydroxide (2:1:1)

(15) Thin-layer chromatography

| Rf value | Solvent |
|---|---|
| 0.56 | Butanol-ethanol-chloroform-17% ammonium hydroxide (4:5:2:5) |
| 0.66 | Chloroform-methanol-17% ammonium hydroxide (1:8:3) |
| 0.16 | A lower layer of chloroform-methanol-17% ammonium hydroxide (2:1:1) |
| 0.76 | An upper layer of chloroform-methanol-17% ammonium hydroxide (2:1:1) |

TLC aluminum sheet (silica gel 60 $F_{254}$ 0.2 mm) (Merck) was used as the plate.

The Rf values by paper chromatography of the novel antibiotics of KA-6606 I, II, III and IV are shown in Table 1 below in comparison with those of known antibiotics. Similar data obtained by thin-layer chromatography are shown in Table 2 below.

TABLE 1

Rf values of the KA-6606 substances and known antibiotics
Solvent system: a lower layer of chloroform-methanol-17% ammonium hydroxide (2:1:1)
Filter paper: Whatman No. 1

| Antibiotics | Rf value |
|---|---|
| KA-6606 I | 0.53 |
| KA-6606 II | 0.86 |
| KA-6606 III | 0.27 |
| KA-6606 IV | 0.55 |
| Gentamicin $C_1$ | 0.59 |
| Gentamicin $C_2$ | 0.35 |
| Gentamicin $C_{1a}$ | 0.12 |
| Sagamicin | 0.49 |
| Sisomicin | 0.12 |
| Verdamicin | 0.35 |
| G-52 | 0.49 |
| Fortimicin A | 0.32 |
| Fortimicin B | 0.89 |
| Others (*1) | 0.0–0.05 |

(*1) Others represent Kanamycin A, B and C, Paromomycin, Neomycin A, B and C, Butirosine A and B, Lividomycin A and B, Ribostamycin, Xylostatin, Gentamicin A and B, Tobramycin, Apramycin, Sorbistin, antibiotic substance 460, Hygromycin, or Destomycin.

TABLE 2

Rf values of the KA-6606 substances and known antibiotics
Solvent system
Solvent I: Butanol-ethanol-chloroform-17% ammonium hydroxide (4:5:2:5)
Solvent II: Chloroform-methanol-17% ammonium hydroxide (1:8:3)
Plate
TLC aluminum sheet (silica gel 60 $F_{254}$ 0.2 mm) (Merck)

| | Rf value | |
|---|---|---|
| Antibiotics | Solvent I | Solvent II |
| KA-6606 I | 0.56 | 0.60 |
| KA-6606 II | 0.57 | 0.52 |
| KA-6606 III | 0.55 | 0.64 |
| KA-6606 IV | 0.56 | 0.66 |
| Gentamicin $C_1$ | 0.52 | 0.40 |
| Gentamicin $C_2$ | 0.51 | 0.44 |
| Gentamicin $C_{1a}$ | 0.43 | 0.34 |
| Sagamicin | 0.45 | 0.32 |
| Fortimicin A | 0.53 | 0.56 |
| Fortimicin B | 0.60 | 0.70 |

The antibiotics spectra of the novel antibiotics KA-6606 I, II, III and IV are shown in Table 3.

TABLE 3

| | KA-6606 substances | | | | Fortimicin | |
|---|---|---|---|---|---|---|
| | I | II | III | IV | A | Amikacin |
| *Staph aureus* 209P | 0.4 | 25 | 3 | 6 | 0.8 | 0.8 |
| SMITH | 0.2 | 12 | 1.5 | 3 | 0.8 | 0.4 |
| *B. anthracis* | 0.2 | 6 | 0.8 | 1.5 | 0.8 | 0.2 |
| cereus | 1.5 | 50 | 6 | 12 | 6 | 1.5 |
| subtilis | 0.2 | 6 | 0.8 | 1.5 | 1.5 | 0.4 |
| *Micrococcus luteus* | 0.4 | >100 | — | — | 6 | 12 |
| *Strept. faecalis* | 25 | >100 | >25 | >50 | 100 | 100 |
| *E. coli* NIHJ | 1.5 | 50 | 12 | 25 | 6 | 3 |
| K-12 ML 1410 | 3 | >100 | >25 | 50 | 12 | 3 |
| K-12 ML 1410 R-81 (I) | 12 | >100 | 25 | >50 | 50 | 12 |
| R-82 (II) | 3 | >100 | 12 | 50 | 12 | 3 |
| R-101 (III) | 3 | >100 | 25 | 50 | 6 | 6 |
| *Prot. vulgaris* OX-19 | 1.5 | 100 | 6 | 6 | 6 | 1.5 |
| *Kleb. pneumoniae* PCI-602 | 1.5 | >100 | 12 | 12 | 6 | 1.5 |
| *Ps. aeruginosa* SHIBATA | 3 | >100 | 25 | 25 | 12 | 0.8 |
| #12 | 0.4 | 100 | 1.5 | 3 | 1.5 | 0.4 |
| TI-13 | 3 | >100 | >25 | >50 | 6 | 1.5 |
| $A_3$ | 3 | >100 | 25 | 50 | 12 | 0.2 |
| K-11 (I) | 6 | >100 | >25 | >50 | 12 | 1.5 |
| 315 (IV) | 6 | >100 | >25 | >50 | 12 | 25 |
| *Providencia sp.* (V) | 1.5 | >100 | 25 | 50 | 6 | 3 | methanol-17% ammonium hydroxide (1:8:3) to elute the KA-6606 III with the above solvent. The corresponding eluted fractions were concentrated under reduced pressure, and lyophilized to afford 70 mg of a white powder of KA-6606 III. Treatment of 794 mg of the crude powder containing KA-6606 IV in the same manner afforded 50 mg of a white powder of KA-6606 IV.

Each of the lyophilized products was dissolved in water, and after adjusting the pH to 7.0, the solution was chromatographed on a column (1×10 cm) of an anion exchange resin, Dowex 1×2 (OH⁻ form), and the active portion was eluted with deionized water. The active fractions were collected and lyophilized to afford 12 mg of KA-6606 III as a pure free base, and 8 mg of KA-6606 IV as a pure free base, respectively.

EXAMPLE 2

A culture medium was prepared from 2% of starch, 1% of soybean meal, 0.5% of corn steep liquor, 0.05% of magnesium sulfate, 0.3% of sodium chloride, 0.3% of calcium carbonate and tap water, adjusted to a pH to 7.0, and sterilized. The KC-6606 strain was inoculated, and cultivated at 27° C. for about 50 hours to form a first seed culture. One hundred milliliters of the first seed culture was transferred to a 20-liter jar fermentor containing 10 liters of the same sterile medium as above. The cultivation was carried out while agitating at 250 rpm at an air flow rate of 10 liters per minute at 27° C. for 4 days.

In the same way as in Example 1, the culture broth was treated, and the desired products were isolated and purified. This procedure resulted in 20 mg of KA-6606 I as a free base, 4 mg of KA-6606 II as a free base, 4 mg of KA-6606 III as a free base, and 5 mg of KA-6606 IV as a free base, all in the purified form.

EXAMPLE 3

Forty milligrams of the KA-6606 I obtained in Example 1 or 2 was dissolved in 1 mol. of 4 N aqueous sodium hydroxide, and the solution was heated for 1 hour. The reaction mixture was dissolved in 100 ml of water, neutralized, and passed through a column (1×10 cm) of a cation exchange resin, Amberlite CG-50 ($NH_4^+$ form). The column was washed with 100 ml of deionized water, and eluted with 1 N ammonium hydroxide. Fractions which had an antibacterial activity and showed a positive result in a ninhydrin reaction were collected, and lyophilized to afford 23 mg of a white powder of KA-6606 II as a free base.

EXAMPLE 4

Forty milligrams of the KA-6606 III obtained in Example 1 or 2 was dissolved in 1 ml of 4 N sodium hydroxide, and the solution was heated for 1 hour. The reaction mixture was dissolved in 100 ml of deionized water, neutralized, and then passed through a column (1×10 cm) of a cation exchange resin, Amberlite CG-50 ($NH_4^+$ form). The column was washed with 100 ml of deionized water, and eluted with 1 N ammonium hydroxide. Fractions which showed a positive result in a ninhydrin reaction and had an antibacterial activity were collected, and lyophilized to afford 18 mg of a white powder of KA-6606 II as a free base.

EXAMPLE 5

Forty milligrams of the KA-6606 IV obtained in Example 1 or 2 was treated in the same way as in Example 3. As a result, 26 mg of a white powder of KA-6606 II was obtained as a free base.

What we claim is:

1. A biologically pure culture of *Saccharopolyspora hirsuta* KC-6606 which has the characteristics identified as FERM P No. 3912 or ATCC 20501 and has the ability to produce an antibiotic KA-6606 by fermentation in nutrient culture medium containing a carbon source, a nitrogen source and minerals.

* * * * *

UNITED STATES PATENT AND TRADEMARK OFFICE
CERTIFICATE OF CORRECTION

PATENT NO. : 4,389,486

DATED : June 21, 1983

INVENTOR(S) : TOSHIHITO MORI; TAKEO DEUSHI; AKIO IWASAKI; TAKAFUMI KUNIEDA; TOSHIMI MIZOGUCHI; KAZUHIRO KAMIYA; MASAHOTO NAKAYAMA; HISAKATSU ITO and TAKESHI ODA It is certified that error appears in the above-identified patent and that said Letters Patent are hereby corrected as shown below:

On the title page of the patent, the first formula appearing in the Abstract, correct to read:

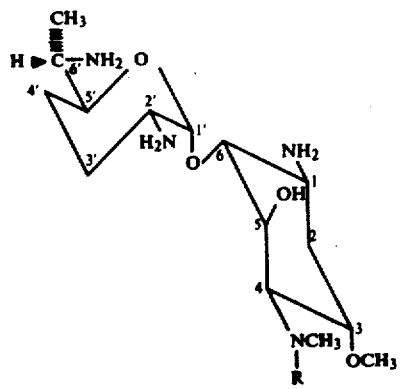

Column 2, correct the formula appearing at lines 1 to 19 to read:

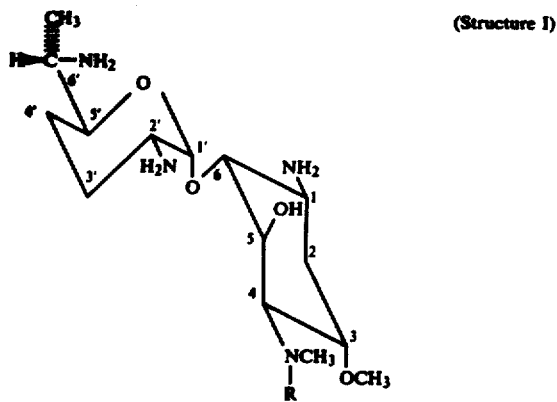

(Structure I)

UNITED STATES PATENT AND TRADEMARK OFFICE
CERTIFICATE OF CORRECTION

PATENT NO. : 4,389,486

DATED : June 21, 1983

INVENTOR(S) : Toshihito Mori et al.

It is certified that error appears in the above-identified patent and that said Letters Patent are hereby corrected as shown below:

Column 2, correct the formula appearing at lines 47 to 65 to read:

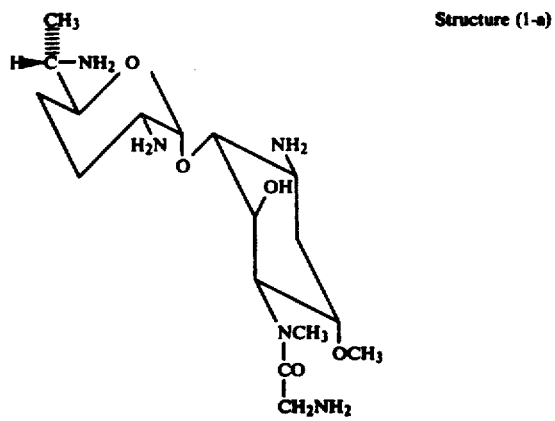

Column 3, correct the formula appearing at lines 9 to 27 to read:

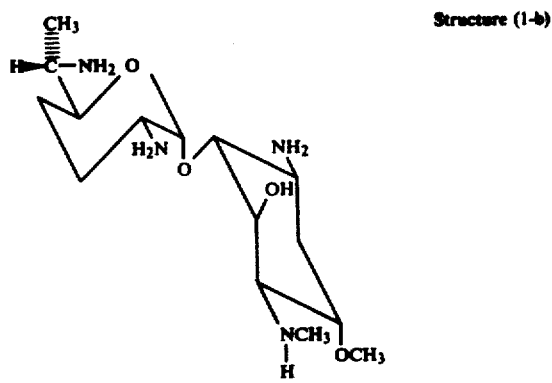

UNITED STATES PATENT AND TRADEMARK OFFICE
CERTIFICATE OF CORRECTION

PATENT NO. : 4,389,486

DATED : June 21, 1983

INVENTOR(S) : Toshihito Mori et al.

It is certified that error appears in the above-identified patent and that said Letters Patent are hereby corrected as shown below:

Column 3, correct the formula appearing at lines 39 to 58 to read:

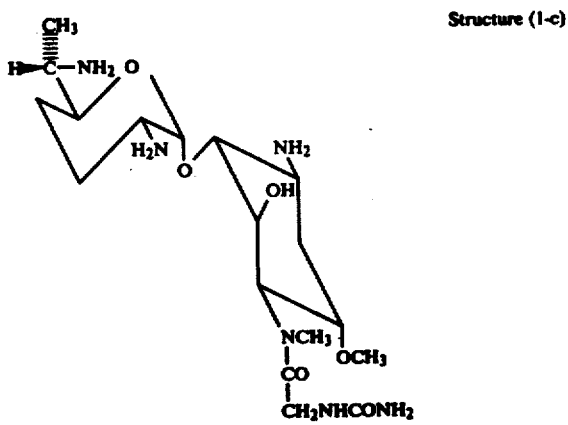

Structure (I-c)

Column 4, correct the formula appearing at lines 1 to 21 to read:

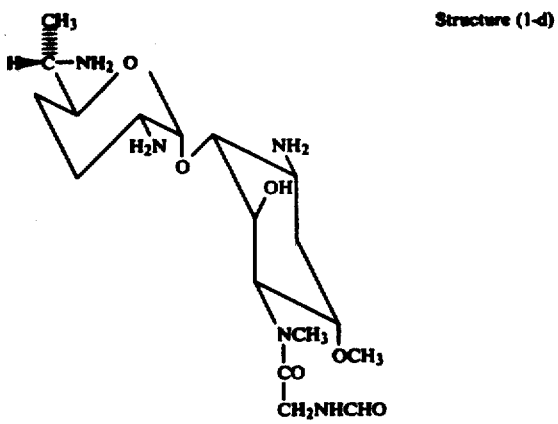

Structure (I-d)

UNITED STATES PATENT AND TRADEMARK OFFICE
CERTIFICATE OF CORRECTION

PATENT NO. : 4,389,486

DATED : June 21, 1983

INVENTOR(S) : Toshihito Mori et al.

It is certified that error appears in the above-identified patent and that said Letters Patent are hereby corrected as shown below:

In Table 3 at the bottom of columns 13 and 14, correct the portion of the table appearing at columns 13 and 14 to read as follows:

Table 3

|  | KA-6606 substances | | | | Fortimicin | |
|---|---|---|---|---|---|---|
|  | I | II | III | IV | A | Amikacin |
| *Staph aureus* 209P | 0.4 | 25 | 3 | 6 | 0.8 | 0.8 |
| SMITH | 0.2 | 12 | 1.5 | 3 | 0.8 | 0.4 |
| *B. anthracis* | 0.2 | 6 | 0.8 | 1.5 | 0.8 | 0.2 |
| cereus | 1.5 | 50 | 6 | 12 | 6 | 1.5 |
| subtilis | 0.2 | 6 | 0.8 | 1.5 | 1.5 | 0.4 |
| *Micrococcus luteus* | 0.4 | >100 | — | — | 6 | 12 |
| *Strept. faecalis* | 25 | >100 | >25 | >50 | 100 | 100 |
| *E. coli* NIHJ | 1.5 | 50 | 12 | 25 | 6 | 3 |
| K-12 ML 1410 | 3 | >100 | >25 | 50 | 12 | 3 |
| K-12 ML 1410 R-81[I] | 12 | >100 | 25 | >50 | 50 | 12 |
| R-82[II] | 3 | >100 | 12 | 50 | 12 | 3 |
| R-101[III] | 3 | >100 | 25 | 50 | 6 | 6 |
| *Prot. vulgaris* OX-19 | 1.5 | 100 | 6 | 6 | 6 | 1.5 |
| *Kleb. pneumoniae* PCI-602 | 1.5 | >100 | 12 | 12 | 6 | 1.5 |
| *Ps. aeruginosa* SHIBATA | 3 | >100 | 25 | 25 | 12 | 0.8 |
| #12 | 0.4 | 100 | 1.5 | 3 | 1.5 | 0.4 |
| TI-13 | 3 | >100 | >25 | >50 | 6 | 1.5 |
| A₃ | 3 | >100 | 25 | 50 | 12 | 0.2 |
| K-11[I] | 6 | >100 | >25 | >50 | 12 | 1.5 |
| 315[IV] | 6 | >100 | >25 | >50 | 12 | 25 |

UNITED STATES PATENT AND TRADEMARK OFFICE
CERTIFICATE OF CORRECTION

PATENT NO. : 4,389,486

DATED : June 21, 1983

INVENTOR(S) : Toshihito Mori et al

It is certified that error appears in the above-identified patent and that said Letters Patent is hereby corrected as shown below:

Column 17, line 39, change "mol." to read --ml.--.

Signed and Sealed this

Twelfth Day of June 1984

[SEAL]

Attest:

GERALD J. MOSSINGHOFF

Attesting Officer

Commissioner of Patents and Trademarks